United States Patent
Marczyk et al.

(10) Patent No.: US 10,064,642 B2
(45) Date of Patent: Sep. 4, 2018

(54) SURGICAL INSTRUMENT FOR DISSECTING TISSUE

(71) Applicant: Covidien LP, Mansfield, MA (US)

(72) Inventors: Stanislaw Marczyk, Stratford, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 14/990,910

(22) Filed: Jan. 8, 2016

(65) Prior Publication Data

US 2016/0256188 A1   Sep. 8, 2016

Related U.S. Application Data

(60) Provisional application No. 62/128,086, filed on Mar. 4, 2015.

(51) Int. Cl.
*A61B 17/3201* (2006.01)
*A61B 17/072* (2006.01)
(Continued)

(52) U.S. Cl.
CPC .... *A61B 17/3201* (2013.01); *A61B 17/07207* (2013.01); *A61B 17/29* (2013.01);
(Continued)

(58) Field of Classification Search
CPC ... A61B 17/3201; A61B 90/03; A61B 17/295; A61B 17/29; A61B 17/07207;
(Continued)

(56) References Cited

U.S. PATENT DOCUMENTS 3,086,288 A   4/1963   Balamuth
3,526,219 A   9/1970   Balamuth
(Continued)

FOREIGN PATENT DOCUMENTS

CA   2440309 A1   10/2002
EP   2130499 A1   12/2009
(Continued)

OTHER PUBLICATIONS

European Office Action dated Aug. 7, 2017, issued in EP Appln. No. 16158375.
(Continued)

*Primary Examiner* — Julian W Woo

(57) ABSTRACT

A surgical instrument includes an end effector supported on a distal end of an elongated shaft, a clamping rod, and a measurement mechanism. The clamping rod extends through the elongated shaft and is operatively associated with the end effector to transition the first and second jaw members between open and clamped positions. The measurement mechanism includes a cylinder, a biasing member, and a locking member. The biasing member is disposed within the cylinder and is disposed over a proximal end of the clamping member distal to a piston disposed at a proximal end of the clamping rod. The cylinder is operatively associated with a moveable handle such that as the moveable handle is moved towards an actuated position, the cylinder is moved proximally such that the biasing member urges the clamping rod proximally to move the first and second jaw members towards the clamped position.

18 Claims, 4 Drawing Sheets

(51) Int. Cl.
*A61B 17/29* (2006.01)
*A61B 17/295* (2006.01)
*A61B 90/00* (2016.01)
A61B 18/14 (2006.01)
A61B 17/00 (2006.01)
A61B 18/00 (2006.01)

(52) U.S. Cl.
CPC ............ *A61B 17/295* (2013.01); *A61B 90/03* (2016.02); *A61B 18/1442* (2013.01); *A61B 2017/00367* (2013.01); *A61B 2017/2922* (2013.01); *A61B 2017/2933* (2013.01); *A61B 2017/2946* (2013.01); *A61B 2018/00607* (2013.01); *A61B 2018/1455* (2013.01); *A61B 2090/034* (2016.02); *A61B 2090/061* (2016.02); *A61B 2090/0807* (2016.02)

(58) Field of Classification Search
CPC ........... A61B 2018/00607; A61B 2017/00367; A61B 2090/061; A61B 2017/2922; A61B 18/1442; A61B 2090/034; A61B 2090/0807; A61B 2018/1455; A61B 2017/2946; A61B 2017/2933
See application file for complete search history.

(56) References Cited

U.S. PATENT DOCUMENTS

| | | |
|---|---|---|
| 3,589,363 A | 6/1971 | Banko et al. |
| 4,312,363 A | 1/1982 | Rothfuss et al. |
| 5,312,330 A | 5/1994 | Klopotek |
| 5,395,385 A | 3/1995 | Kilmer et al. |
| 5,441,512 A | 8/1995 | Muller |
| 5,643,248 A * | 7/1997 | Yoon .............. A61B 17/320016 606/1 |
| 6,099,541 A | 8/2000 | Klopotek |
| 6,126,668 A | 10/2000 | Bair et al. |
| 6,280,407 B1 | 8/2001 | Manna et al. |
| 6,863,677 B2 | 3/2005 | Breznock |
| 7,367,939 B2 | 5/2008 | Smith et al. |
| 7,497,866 B2 | 3/2009 | Perez |
| 7,534,242 B2 | 5/2009 | Buehlmann et al. |
| 7,766,910 B2 * | 8/2010 | Hixson .............. A61B 18/1445 606/45 |
| 7,833,233 B2 | 11/2010 | Mueller et al. |
| 8,002,788 B2 | 8/2011 | Heinrich et al. |
| 8,460,316 B2 | 6/2013 | Wilson et al. |
| 9,259,232 B2 * | 2/2016 | Esanu .................. A61B 17/122 |
| 2004/0220599 A1 | 11/2004 | Pallikaris et al. |
| 2005/0250986 A1 | 11/2005 | Rothe et al. |
| 2006/0173481 A1 | 8/2006 | Thorson |
| 2007/0265649 A1 | 11/2007 | Perez |
| 2008/0125803 A1 | 5/2008 | Sadamasa et al. |
| 2008/0275471 A1 * | 11/2008 | Viola .................. A61B 17/128 606/142 |
| 2009/0198180 A1 | 8/2009 | Buehlmann et al. |
| 2010/0198248 A1 | 8/2010 | Vakharia |
| 2012/0022527 A1 | 1/2012 | Woodruff et al. |
| 2012/0080484 A1 * | 4/2012 | Morgan .................. A61B 90/92 227/176.1 |
| 2012/0109184 A1 | 5/2012 | Spivey et al. |

FOREIGN PATENT DOCUMENTS

| | | |
|---|---|---|
| GB | 2496735 A | 5/2013 |
| WO | 2010104755 A1 | 9/2010 |
| WO | 2015025745 A1 | 2/2015 |

OTHER PUBLICATIONS

European Search Report dated Jul. 13, 2016, issued in European Application No. 16158375.2.

* cited by examiner

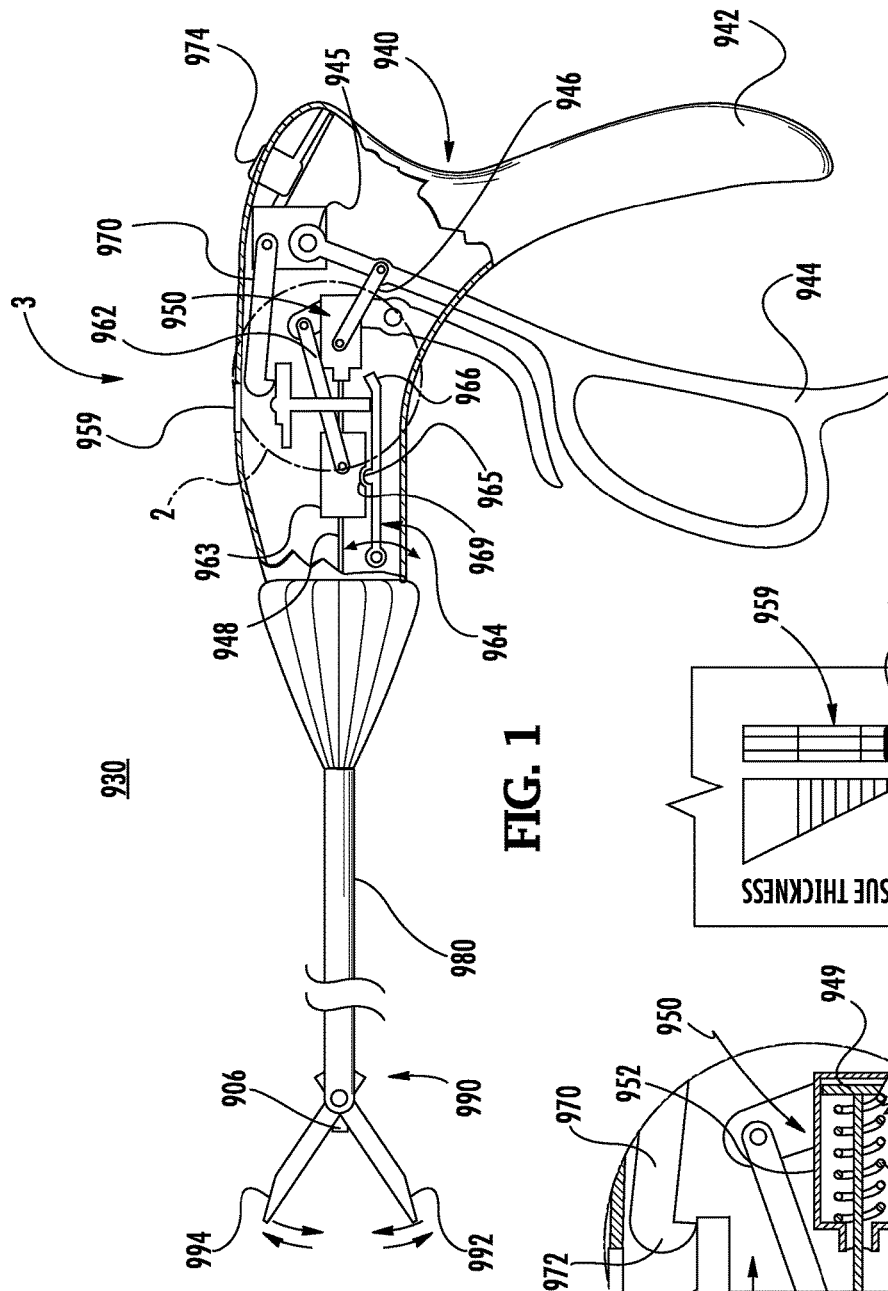

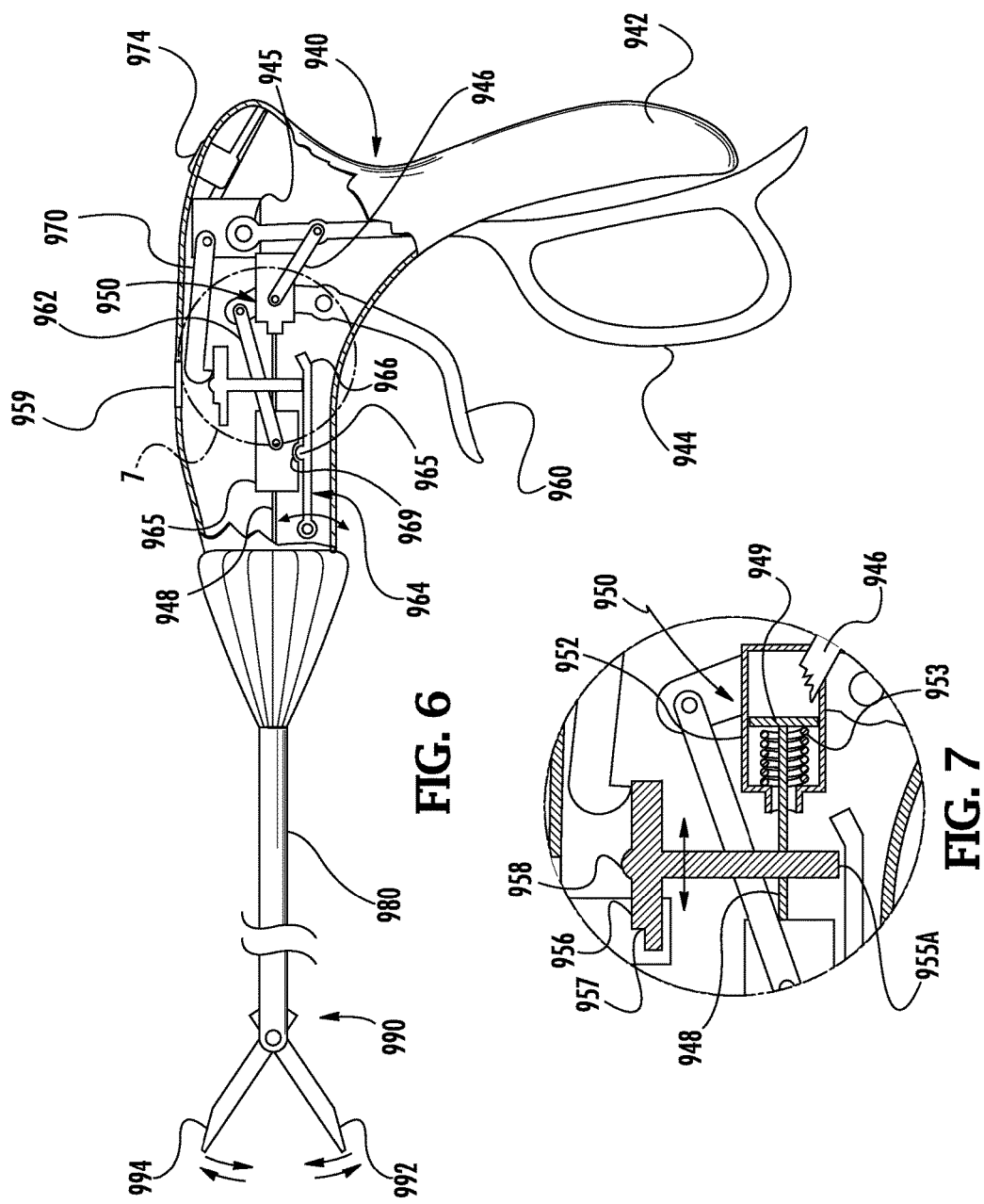

SURGICAL INSTRUMENT FOR DISSECTING TISSUE

CROSS-REFERENCE TO RELATED APPLICATIONS

This application claims the benefit of and priority to U.S. Provisional Patent Application No. 62/128,086 filed Mar. 4, 2015, the entire disclosure of which is incorporated by reference herein.

BACKGROUND

1. Technical Field

The present disclosure relates to surgical instruments, and, more specifically, to surgical instruments for dissecting tissue.

2. Background of Related Art

Abdominal surgery is known to be a contributor in the development of abdominal adhesions. Abdominal adhesions are bands of scar tissue that form between abdominal tissues and organs that cause tissues and organs to adhere together. These adhesions can range from being flimsy like "cobwebs" or being dense as "concrete", causing complications to the patient years after the surgery is performed.

Conventional methods for dissecting abdominal adhesions include surgery. However, subsequent abdominal surgeries increase the risk that additional adhesions will occur. In addition, during a dissection procedure a surgeon risks accidental cutting or puncturing of an underlying organ. Thus, most surgeons only remove adhesions if they interrupt the surgical field or interfere with the procedure.

A concern for dissecting or reducing adhesions is the time taken and the difficulty as the density of the adhesion increases. One delay is the tedious task of manual dissection which must be performed in order to reveal obscured sections of bowel. Depending on the adhesion, the surgeon may use a different surgical instrument to dissect each type of adhesion. For example, for a flimsy adhesion a scissors or a blunt dissection instrument may be used and for a dense adhesion an electro-cautery instrument or an ultrasonic instrument may be used.

Accordingly, there is a continuing need for improved surgical instruments that reduce delays during procedures to remove adhesions.

SUMMARY

In an aspect of the present disclosure, a surgical instrument includes a body, an elongated shaft extending from the body, an end effector, a clamping rod, a moveable handle, and a measurement mechanism. The end effector is disposed at and supported on the distal end of the elongated shaft. The end effector includes first and second jaw members that are moveable relative to one another between open and clamped positions. The clamping rod extends through the elongated shaft from within the body and is operatively associated with the end effector to transition the first and second jaw members between the open and clamped positions. The clamping rod has a piston that is disposed at a proximal end thereof. The moveable handle is pivotally mounted to the body and is pivotable between unactuated and actuated positions. The measurement mechanism includes a cylinder, a biasing member, and a locking member. The biasing member is disposed within the cylinder and is disposed over the proximal end of the clamping rod distal to the piston. The cylinder is operatively associated with the moveable handle such that as the moveable handle is moved towards the actuated position, the cylinder is moved proximally such that the biasing member urges the clamping rod proximally. As the clamping rod is moved proximally, the clamping rod moves the first and second jaw members towards the clamped position.

In aspects, the biasing member is configured to prevent the first and second jaw members from clamping tissue greater than a predetermined tissue thickness. The biasing member may be configured to compress between the piston and the cylinder when the first and second jaw members are positioned over tissue having a thickness greater than the predetermined tissue thickness as the moveable handle is moved towards the actuated position.

In some aspects, the measurement mechanism includes a clamp indicator/locking member that is fixed to the clamping rod distal to the cylinder. The clamp indicator/locking member may include indicia of the position of the clamping rod relative to the body. The position of the clamping rod relative to the body may be indicative of the thickness of tissue between the first and second jaw members.

In certain aspects, the instrument includes a lever for advancing a knife through tissue clamped between the first and second jaw members. The instrument may include a knife tube that is disposed over the clamping rod. The knife tube may be operatively associated with the knife such that advancement of the knife tube relative to the body advances the knife. The lever may be operatively coupled to the knife tube to advance the knife as the lever is pivoted towards the fixed handle. The instrument may include a knife lockout that has a locking tab. The knife tube may define a locking notch and the knife lockout may be biased towards the knife tube such that the locking tab is received within the locking notch to prevent advancement of the knife. The knife lockout may include a release cam that is engaged by the clamp indicator/locking member when the clamping rod is retracted to a clamped position to disengage the locking tab of the knife lockout from the locking notch of the knife tube to permit the knife tube to advance the knife. The knife lockout may be configured to prevent advancement of the knife when the first and second jaw members are in the open position.

In particular aspects, the instrument includes a clamp lock and the clamp indicator/locking member includes a clamp locking notch that is engagable by the clamp lock when the first and second jaw members are in the clamped position. The clamp lock may secure the first and second jaw members in the clamped position. The instrument may include a clamp release switch that is engagable to move the clamp lock out of engagement with the clamp locking notch.

In another aspect of the present disclosure, a method for severing tissue includes position tissue between first and second jaw members of a surgical instrument, pivoting a moveable handle of the surgical instrument to an actuated position, and actuating a lever to advance a knife through tissue between the first and second jaw members. The surgical instrument may be any of the surgical instruments disclosed herein.

In aspects, the method includes verifying the thickness of the tissue between the first and second jaw members after pivoting the moveable handle to the actuated position through a window defined by the surgical instrument. Verifying the thickness of the tissue may include observing the position of a tissue thickness indicator through the window. The tissue thickness indictor may be fixed relative to the clamping rod to provide indicia of the position of the clamping rod relative to a body of the surgical instrument.

In some aspects, pivoting the moveable handle to the actuated position includes the first and second jaw members compressing tissue between the first and second jaw members in response to the clamping rod being urged proximally by the clamping rod biasing member. The clamping rod biasing member may be compressed in response to a thickness of the tissue being clamped.

In certain aspects, pivoting the moveable handle to the actuated position includes locking the clamping rod in the clamped position. Locking the clamping rod in the clamped position may include locking the clamping rod with a clamp lock. Locking the clamping member in the clamped position may include a clamp lock engaging the clamp indicator/locking member that is fixed to the clamping rod. The clamp indicator/locking member may engage a knife lockout to permit a knife tube to advance when the clamping rod is in the clamped position.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a side view of an embodiment of a surgical instrument provided in accordance with the present disclosure with a portion of the body of the surgical instrument removed;

FIG. 2 is an enlarged view of the indicated area of detail of FIG. 1;

FIG. 3 is a partial top view of the surgical instrument of FIG. 1;

FIG. 6 is a side view of the instrument of FIG. 1 with the moveable handle pivoted and the end effector in an open position; and FIG. 7 is an enlarged view of the indicated area of detail of FIG. 6.

DETAILED DESCRIPTION

Figure 4:
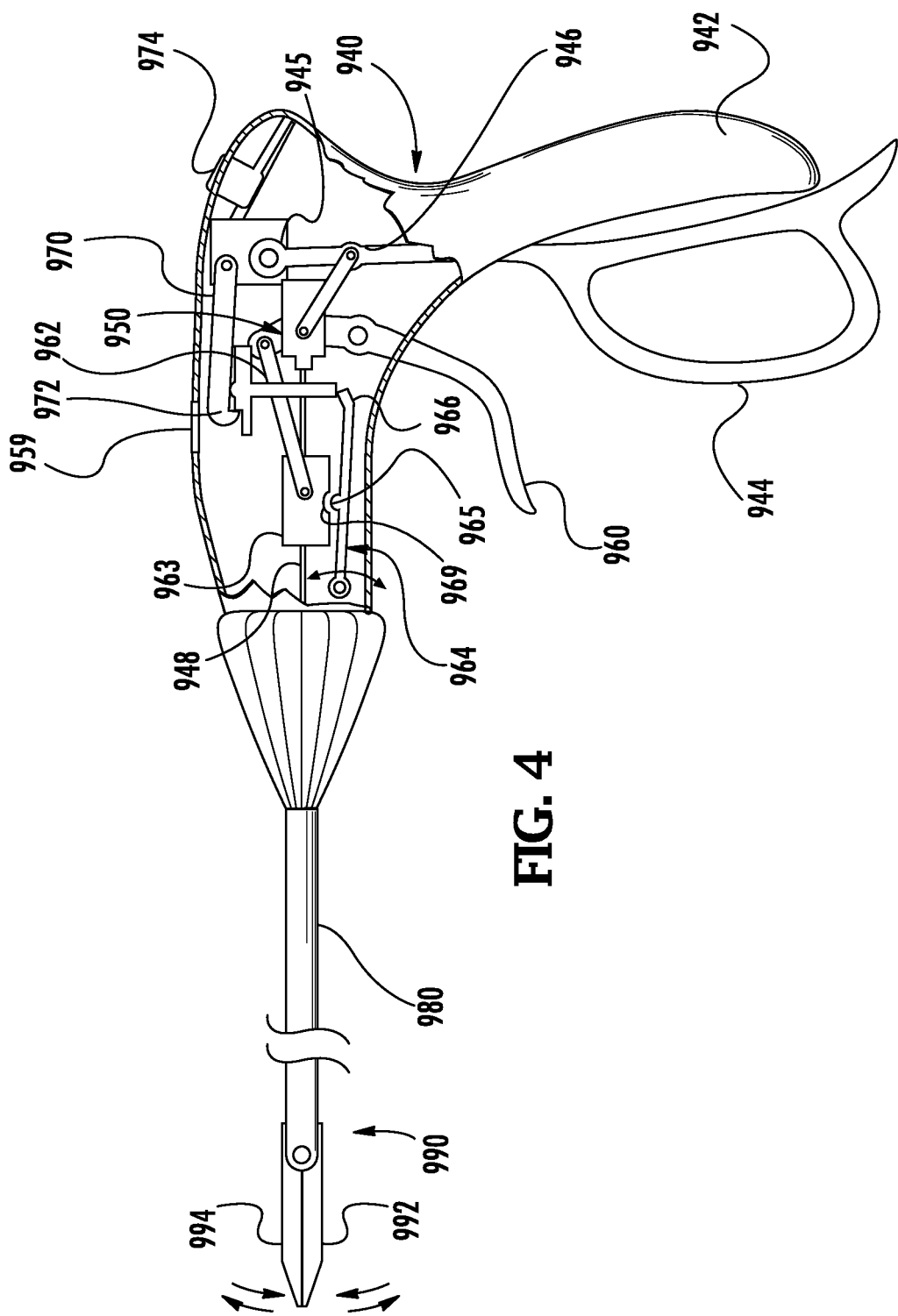
FIG. 4 is a side view of the instrument of FIG. 1 with a moveable handle pivoted and the end effector in a clamped position.
Figure 5:
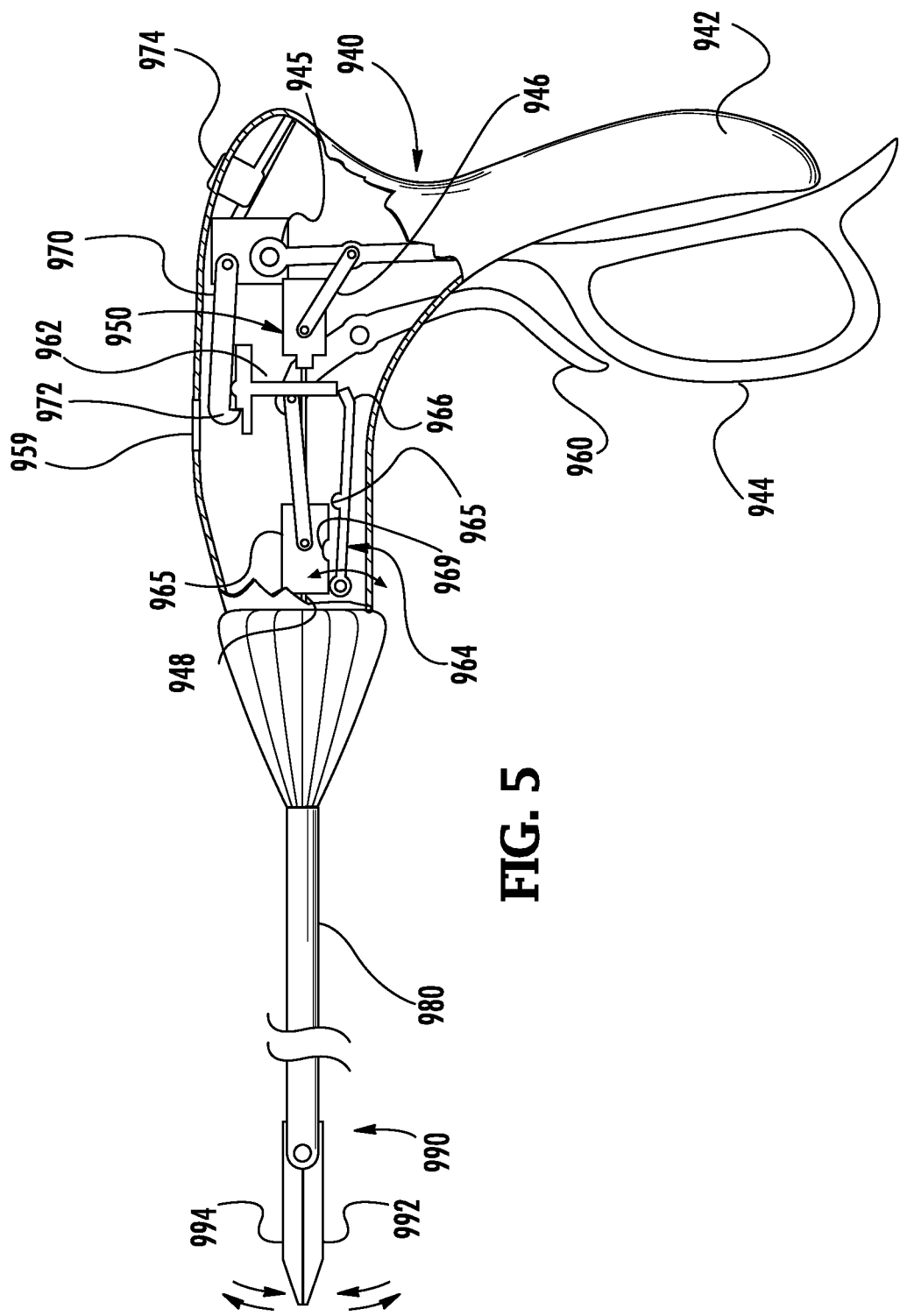
FIG. 5 is a side view of the instrument of FIG. 1 with the moveable handle pivoted and the cutting lever pivoted.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring to FIG. 1, a surgical instrument 930 is provided in accordance with the present disclosure and includes a body 940 and an elongate shaft 980 extending from the body 940 to an end effector 990. The surgical instrument 930 includes a mechanical tissue thickness indicator 958 (FIG. 3) to provide visual indicia to a user of the thickness of tissue grasped within the end effector 990 as detailed below.

The end effector 990 includes first and second jaws 992, 994 that are moveable relative to one another between an open position (FIG. 1) and a clamped position (FIG. 4). The surgical instrument 930 includes a clamping rod 948 slidably disposed within the elongate shaft 980 that operatively associates the end effector 990 with a moveable handle 944 of the body 940 as detailed below. When the clamping rod 948 is translated proximally, the clamping rod 948 moves the end effector 990 towards the clamped position and when the clamping rod 948 is translated distally, the clamping rod 948 moves the end effector 990 towards the open position. The clamping rod 948 includes a piston 949 (FIG. 2) positioned at a proximal end of the clamping rod 948.

With continued reference to FIG. 1, the body 940 includes a fixed handle 942, a moveable handle 944, and a lever 960. The moveable handle 944 and the lever 960 are separately biased away from the fixed handle 942 to an unactuated or spaced apart position. The moveable handle 944 is coupled to a tissue thickness measurement mechanism 950 by a clamping link 946. The measurement mechanism 950 operatively couples the moveable handle 944 to the clamping rod 948 and provides a user with indicia of the thickness of tissue grasped within the end effector 990 as the moveable handle 944 is pivoted towards the fixed handle 942. In addition, the measurement mechanism 950 releases a knife lockout 964 to permit a user to actuate the lever 960 as detailed below.

The measurement mechanism 950 includes a cylinder 952, a clamping rod biasing member 953, and a clamp indicator/locking member 954. The cylinder 952 is disposed over the proximal end of the clamping rod 948 to enclose the clamping piston 949 therein. The clamping rod biasing member 953 is disposed within the cylinder 952 and over the clamping rod 948. The clamping rod biasing member 953 is positioned between a distal surface of the cylinder 952 and the clamping piston 949 such that the clamping rod biasing member 953 urges the clamping rod 948 proximally.

The measurement mechanism 950 is calibrated to limit the clamping force and/or prevent the end effector 990 from grasping tissue that has a thickness greater than a predetermined tissue thickness. When the moveable handle 944 is pivoted towards the fixed handle 942, the moveable handle 944 translates the cylinder 952 proximally within the body 940. As the cylinder 952 moves proximally, the distal surface of the cylinder 952 moves the clamping rod biasing member 953 proximally such that the clamping rod biasing member 953 engages the clamping piston 949 to apply a clamping force to the clamping piston 949. When the clamping rod biasing member 953 applies the clamping force to the clamping piston 949, the clamping force is applied to the first and second jaws 992, 994 of the end effector 990 to move the end effector 990 towards the clamped position. If tissue within the end effector 990 is thin or compressible, the clamping force is greater than or equal to a force required to move the jaw members 992, 994 to the clamped position (i.e., the clamping rod 948 moves proximally with the cylinder 952). When the end effector 990 reaches the clamped position, a clamp locking member 970 may engage the clamp indicator/locking member 954 to fix the end effector 990 in the clamped position as detailed below. It will be appreciated that the clamping force may increase linearly or exponentially as the moveable handle 944 is pivoted towards the fixed handle 942.

If the clamping force is less than a force required to move the jaw members 992, 994 to the clamped position (e.g., the tissue is uncompressible and/or has a thickness greater than the predetermined thickness) the clamping piston 949 resists proximal translation as the cylinder 952 is moved proximally and thus, the clamping rod biasing member 953 is compressed between the distal surface of the cylinder 952 and the clamping piston 949. If tissue within the end effector 990 is greater than a predetermined tissue thickness, the moveable handle 944 fully pivots to a position adjacent the fixed handle 942 without the end effector 990 reaching the clamped position. It will be appreciated that if the end effector 990 does not reach the clamped position, the clamp locking member 970 does not engage the clamp indicator/locking member 954.

The clamp indicator/locking member 954 is fixed to the clamping rod 948, distal to the cylinder 952, such that the member 954 is translated with the clamping rod 948. The member 954 includes a vertical support or shaft 955 that is coupled to the clamping rod 948 and orientated orthogonal to the clamping rod 94 such that a portion of the vertical shaft 955 extends above and below the clamping rod 948. The vertical shaft 955 includes a lock release 955a that extends below the clamping rod 948 and towards a knife lockout 964 (FIG. 2). In addition, the vertical shaft 955 includes a clamp locking member 956 that is fixed to an upper end of the vertical shaft 955. The clamp locking member 956 is substantially parallel to the clamping rod 948. The clamp locking member 956 defines a clamp locking notch 957 and includes a tissue thickness indicator 958. The tissue thickness indicator 958 provides visual indicia of the longitudinal position of the clamping rod 948 relative to the body 940. As shown in FIG. 3, the body 940 defines a window 959 and the indicator 958 is aligned with the window 959 such that a user may determine the longitudinal position of the clamping rod 948 relative to the body 940. As shown, the body 940 may include visual indicia related to the thickness of tissue grasped within the end effector 990 in response to a viewing of the indicator 958 through the window 959.

When the end effector 990 reaches the clamped position, the clamping rod 948 is positioned such that the clamp lock 970 engages the clamp locking member 956 to prevent the end effector 990 from moving towards the open position by preventing the clamping rod 948 from moving distally. When the clamping rod 948 is prevented from moving distally, the end effector 990 is secured in the clamped position. The clamp lock 970 may include a distal finger 972 that is configured to engage the clamp locking notch 957 of the clamp locking member 956. The clamp lock 970 is associated with a clamp release switch 974 that is disposed on the body 940. The clamp release switch 974 is selectively engagable to pivot the clamp lock 970 out of engagement with the clamp locking member 956 and thus, permit the end effector 990 to move from the clamped position towards the open position.

With particular reference to FIGS. 1 and 2, the lever 960 is pivotable relative to the body 940 about a pivot 961 to advance a knife 906 through tissue clamped within the end effector 990. The lever 960 is operatively coupled to a knife tube 963 that is disposed over the clamping rod 948 by a knife link 962. The knife link 962 is coupled at one end to the lever 960 and on the other end to the knife tube 963.

The lever 960 is prevented from pivoting to advance the knife when the end effector 990 is in the open position or when tissue grasped within the end effector 990 is greater than a predetermined thickness limit by a knife lockout 964. The knife lockout 964 is pivotally disposed within the body 940 and includes a locking tab 965 and a release cam 966. The knife lockout 964 is biased towards the knife tube 963 such that the locking tab 965 is urged towards the locking notch 969. When the locking tab 965 is received within the locking notch 969, the lever 960 is prevented from pivoting to advance the knife 906 through tissue grasped within the end effector 990. As shown in FIG. 4, the release cam 966 is engagable by the lock release 955a of the vertical shaft 955 to move the knife lockout 964 such that the locking tab 965 is moved out of the locking notch 969. When the locking tab 965 is out of engagement with the locking notch 969, the lever 960 may be pivoted to advance the knife through tissue grasped within the end effector 990.

Referring to FIGS. 1-7, the use of instrument 930 is detailed in accordance with the present disclosure. The surgical instrument 930 is provided with the moveable handle 944 spaced apart from the fixed handle 942 and the locking tab 965 of the knife lockout 964 positioned within the locking notch 969 such that the locking lever 960 is spaced apart from the fixed handle 942 as shown in FIGS. 1 and 2. It will be appreciated, when the moveable handle 944 is spaced apart from the fixed handle 942, the end effector 990 is in the open position.

The instrument 930 is positioned such that tissue to be grasped and severed is positioned within the end effector 990. With the tissue positioned within the end effector 990, the moveable handle 944 is moved towards the fixed handle 942. As the moveable handle is moved towards the fixed handle 942, the moveable handle 944 translates the cylinder 952 proximally such that a clamping force is applied to the clamping piston 949 to move the end effector 990 towards the clamped position. As the clamping force is applied to the clamping piston 949, the first and second jaws 992, 994 engage the tissue disposed within the end effector 990. As the first and second jaws 992, 994 engage the tissue, the clamping rod biasing member 953 compresses to prevent excessive clamping force from being applied to the tissue within the end effector 990. When the moveable handle 944 is fully actuated or compressed and the tissue within the end effector 990 has a thickness less than or equal to the predetermined thickness, the clamping rod 948 is translated proximally within the body 940 such that the clamp lock 970 engages the clamp locking member 956 and the tissue thickness indicator 958 (FIG. 3) is positioned within the sever range, of a tissue thickness gauge located in the upper surface of the body 940. With particular reference to FIG. 4, when the clamping rod 948 is translated proximally, the lock release 955a of the vertical shaft 955 engages the lock release cam 966 of the knife lockout 964 to move the locking tab 965 out of the locking notch 969.

With the end effector 990 secured in the clamped position and the locking tab 965 out of the locking notch 969, a clinician may release the moveable handle 944 and actuate or pivot the lever 960 towards the fixed handle 942 to translate the knife tube 963 distally to advance the knife 906 and sever tissue clamped within the end effector 990. After the knife 906 is advanced through the tissue, the clinician may release the lock lever 960. The lock lever 960 may be biased towards the unactuated position such that when the lock lever 960 is released, the knife 906 is retracted within the end effector 990. A safety mechanism (not shown) may prevent actuation of the clamp release switch 974 unless the knife is retracted.

Specifically, after the knife 906 has been retracted, the clinician may then engage the clamp release switch 974 to move the clamp lock 970 out of engagement with the clamp locking member 956 such that the clamp locking member 956 is released. When the clamp locking member 956 is released, the clamp biasing member 953 urges cylinder 952 distally to move the moveable handle 944 towards the unactuated position spaced apart from the fixed handle 942. It will be appreciated that as the moveable handle 944 moves towards the unactuated position, the clamping rod 948 moves distally to move the jaws 992, 994 of the end effector 990 towards the open position.

With reference to FIGS. 6 and 7, when the moveable handle 944 is fully actuated or compressed, if the tissue within the end effector 990 has a thickness greater than the predetermined thickness, the clamping rod biasing member 953 is compressed between the distal surface of the cylinder 953 and the clamping piston 949 such that the clamping rod 948 is not translated proximally within the body 940 to a position engagable by the clamp lock 970. In addition, the tissue thickness indicator 958 (FIG. 42) is positioned within the thick tissue portion of the tissue thickness gauge, located in the upper surface of the body 940. This may indicate that the tissue within the end effector 990 is an organ (e.g., bowel). When the clinician releases the moveable handle 944, the clamping rod biasing member 953 returns the moveable handle 944 to the unactuated position as detailed above such that the clinician may reposition the instrument 930.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument comprising:
   a body;
   an elongated shaft extending from the body;
   an end effector disposed at and supported on the distal end of the elongated shaft, the end effector including first and second jaw members moveable relative to one another between an open position and a clamped position;
   a clamping rod extending from within the body, through the elongated shaft, and operatively associated with the end effector to transition the first and second jaw members between the open and clamped positions, the clamping rod having a piston disposed at a proximal end thereof;
   a moveable handle pivotally mounted to the body and pivotable between an unactuated position and an actuated position;
   a measurement mechanism including a cylinder, a biasing member, and a locking member, the biasing member disposed within the cylinder and disposed over the proximal end of the clamping rod distal to the piston, the cylinder pivotally coupled with the moveable handle such that as the moveable handle is moved towards the actuated position, the cylinder is moved proximally such that the biasing member urges the clamping rod proximally to move the first and second jaw members towards the clamped position.

2. The instrument of claim 1, wherein the biasing member is configured to prevent the first and second jaw members from clamping tissue greater than a predetermined tissue thickness, the biasing member configured to compress between the piston and the cylinder when the first and second jaw members are positioned over tissue having a thickness greater than the predetermined tissue thickness as the moveable handle is moved towards the actuated position.

3. The instrument of claim 1, wherein the measurement mechanism includes a clamp indicator/locking member fixed to the clamping rod distal to the cylinder, the clamp indicator/locking member including indicia of the position of the clamping rod relative to the body.

4. The instrument of claim 3, wherein the position of the clamping rod relative to the body is indicative of the thickness of tissue between the first and second jaw members.

5. The instrument of claim 3, further comprising a lever for advancing a knife through tissue clamped between the first and second jaw members.

6. The instrument of claim 5, further comprising a knife tube disposed over the clamping rod and being operatively associated with the knife, wherein advancement of the knife tube relative to the body advances the knife, and wherein the lever operatively coupled to the knife tube advances the knife as the lever is pivoted towards the fixed handle.

7. A surgical instrument comprising:
   a body;
   an elongated shaft extending from the body;
   an end effector disposed at and supported on the distal end of the elongated shaft, the end effector including first and second jaw members moveable relative to one another between an open position and a clamped position;
   a clamping rod extending from within the body, through the elongated shaft, and operatively associated with the end effector to transition the first and second jaw members between the open and clamped positions, the clamping rod having a piston disposed at a proximal end thereof;
   a moveable handle pivotally mounted to the body and pivotable between an unactuated position and an actuated position;
   a measurement mechanism including a cylinder, a biasing member, a locking member, and a clamp indicator/locking member, the biasing member disposed within the cylinder and disposed over the proximal end of the clamping rod distal to the piston, the cylinder operatively associated with the moveable handle such that as the moveable handle is moved towards the actuated position, the cylinder is moved proximally such that the biasing member urges the clamping rod proximally to move the first and second jaw members towards the clamped position, the clamp indicator/locking member fixed to the clamping rod distal to the cylinder, the clamp indicator/locking member including indicia of the position of the clamping rod relative to the body;
   a lever for advancing a knife through tissue clamped between the first and second jaw members;
   a knife tube disposed over the clamping rod and being operatively associated with the knife, wherein advancement of the knife tube relative to the body advances the knife, and wherein the lever operatively coupled to the knife tube advances the knife as the lever is pivoted towards the fixed handle; and
   a knife lockout having a locking tab, the knife tube defining a locking notch, wherein the knife lockout is biased towards the knife tube such that the locking tab is received within the locking notch to prevent advancement of the knife.

8. The instrument of claim 7, wherein the knife lockout includes a release cam that is engaged by the clamp indicator/locking member when the clamping rod is retracted to a clamped position to disengage the locking tab of the knife lockout from the locking notch of the knife tube to permit the knife tube to advance the knife.

9. The instrument of claim 7, wherein the knife lockout is configured to prevent advancement of the knife when the first and second jaw members are in an open position.

10. A surgical instrument comprising:
a body;
an elongated shaft extending from the body;
an end effector disposed at and supported on the distal end of the elongated shaft, the end effector including first and second jaw members moveable relative to one another between an open position and a clamped position;
a clamping rod extending from within the body, through the elongated shaft, and operatively associated with the end effector to transition the first and second jaw members between the open and clamped positions, the clamping rod having a piston disposed at a proximal end thereof;
a moveable handle pivotally mounted to the body and pivotable between an unactuated position and an actuated position;
a measurement mechanism including a cylinder, a biasing member, a locking member, and a clamp indicator/locking member, the biasing member disposed within the cylinder and disposed over the proximal end of the clamping rod distal to the piston, the cylinder operatively associated with the moveable handle such that as the moveable handle is moved towards the actuated position, the cylinder is moved proximally such that the biasing member urges the clamping rod proximally to move the first and second jaw members towards the clamped position, the clamp indicator/locking member fixed to the clamping rod distal to the cylinder, the clamp indicator/locking member including indicia of the position of the clamping rod relative to the body; and
a clamp lock and the clamp indicator/locking member includes a clamp locking notch engagable by the clamp lock when the first and second jaw members are in the clamped position to secure the first and second jaw members in the clamped position.

11. The instrument of claim 10, further including a clamp release switch that is engagable to move the clamp lock out of engagement with the clamp locking notch.

12. A method for severing tissue, the method comprising:
positioning tissue between first and second jaw members of a surgical instrument;
pivoting a moveable handle of the surgical instrument to an actuated position, the moveable handle coupled to a cylinder by a link to move the cylinder proximally as the moveable handle is pivoted proximally, the cylinder including a clamping rod biasing member that urges the clamping rod proximally as the cylinder is moved proximally to move the first and second jaw members towards a clamped position; and
actuating a lever to advance a knife through the tissue between the first and second jaw members, the lever coupled to a knife tube disposed over the clamping rod.

13. The method of claim 12, further including verifying the thickness of the tissue between the first and second jaw members after pivoting the moveable handle to the actuated position through a window defined by the surgical instrument.

14. The method of claim 13, wherein verifying the thickness of the tissue includes observing the position of a tissue thickness indicator through the window, the tissue thickness indicator fixed relative to the clamping rod to provide indicia of the position of the clamping rod relative to a body of the surgical instrument.

15. The method of claim 14, wherein pivoting the moveable handle to the actuated position includes the first and second jaw members compressing tissue between the first and second jaw members in response to the clamping rod being urged proximally by the clamping rod biasing member, the clamping rod biasing member compressing in response to a thickness of the tissue being clamped.

16. The method of claim 12, wherein pivoting the moveable handle to the actuated position includes locking the clamping rod in the clamped position.

17. The method of claim 16, wherein locking the clamping rod in the clamped position includes locking the clamping rod with a clamp lock.

18. The method of claim 16, wherein locking the clamping rod in the clamped position includes a clamp lock engaging a clamp indicator/locking member fixed to the clamping rod, the clamp indicator/locking member engaging a knife lockout to permit a knife tube to advance when the clamping rod is in the clamped position.

* * * * *